United States Patent [19]

Kuekenhoehner et al.

[11] Patent Number: 5,473,069

[45] Date of Patent: Dec. 5, 1995

[54] PREPARATION OF ISOXAZOLE-4,5-DICARBOXYLIC DIESTERS

[75] Inventors: Thomas Kuekenhoehner, Frankenthal; Volker Maywald, Ludwigshafen, both of Germany

[73] Assignee: BASF Aktiengesellschaft, Ludwigshafen, Germany

[21] Appl. No.: 667,134

[22] Filed: Mar. 11, 1991

[30] Foreign Application Priority Data

Mar. 21, 1990 [DE] Germany .......................... 40 09 028.0

[51] Int. Cl.$^6$ ................................................ C07D 261/12
[52] U.S. Cl. ....................... 544/238; 544/333; 544/367; 544/405; 546/209; 546/275; 548/236; 548/248
[58] Field of Search ............................... 548/248; 544/238

[56] References Cited

U.S. PATENT DOCUMENTS

| | | | |
|---|---|---|---|
| 3,073,839 | 1/1963 | Kano et al. | 548/248 |
| 4,190,728 | 2/1980 | Adachi | 548/248 |
| 4,952,700 | 8/1990 | Markofsky et al. | 548/248 |
| 5,080,708 | 1/1992 | Freund et al. | 548/248 |

FOREIGN PATENT DOCUMENTS

| | | | |
|---|---|---|---|
| 2754832 | 6/1979 | Germany . | |
| 3932915 | 4/1990 | Germany . | |
| 2155471 | 9/1985 | United Kingdom | 548/248 |

OTHER PUBLICATIONS

Royals, Advanced Organic Chemistry, p. 527, Prentice-Hall, Inc., 1954.
Fieser, Organic Chemistry, pp. 82–83, D. C. Heath and Co., 1950.
Yokoyama et al. Tetrahedron Letters vol. 30 pp. 3675–3676(1989).
Harada et al. Chem. Pharm Bull. vol. 28, pp. 3296–3303 (1980).
Graboloski et al. Chem Abstr vol. 104 Entry 129708g (1986) abstracting Polish 122813.
McKillop Tetrahedron, vol. 30, pp. 1365–1371 (1974).
Kajio et al. Chem. Pharm. Bull. 26 (1978) 3254–3256.
Shimizu et al. Bull. Chem. Soc. Jpn. 59 (1986) 2827–2831.
Shimizu et al. Bull. Chem. Soc. Jpn. 57,(1984) 2531–2534.
Lee Synthesis (1982) 508–9.

*Primary Examiner*—Donald G. Daus
*Attorney, Agent, or Firm*—Keil & Weinkauf

[57] ABSTRACT

The preparation of isoxazole-4,5-dicarboxylic diester of the formula I

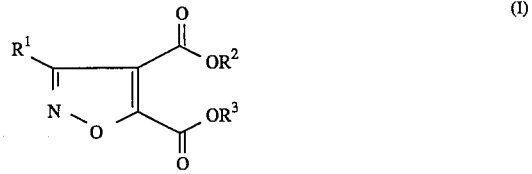

where $R^1$ is any organic radical which is inert under the reaction conditions, and $R^2$ and $R^3$ are each alkyl, cycloalkyl or benzyl, entails reacting an aldoxime of the formula II

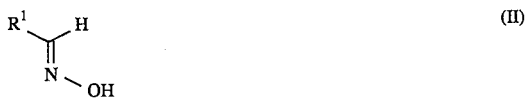

with a diester of maleic or fumaric acid, of the formula III

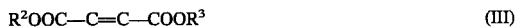

where $R^2$ and $R^3$ are identical or different and have the abovementioned meanings, in the presence of an aqueous solution of a hypohalite which is present in excess relative to II.

7 Claims, No Drawings

PREPARATION OF ISOXAZOLE-4,5-DICARBOXYLIC DIESTERS

The present invention relates to a process for preparing isoxazole-4,5-dicarboxylic diesters of the formula I

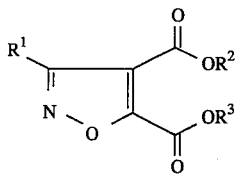

where $R^1$ is any organic radical which is inert under the reaction conditions, and $R^2$ and $R^3$ are each alkyl, cycloalkyl or benzyl.

The present invention also relates to novel isoxazole derivatives which are used as intermediates in organic syntheses, in particular for preparing crop protection agents.

It is known from the literature that isoxazole- 4,5-dicarboxylic diesters can be prepared by 1,3-dipolar cycloaddition of nitrile oxides IV onto activated triple bonds, eg. acetylenedicarboxylic diesters, according to the following equation (a) (see, for example, Chem. Pharm. Bull. 26 (1978) 3254–3256). The corresponding reaction with activated double bonds, on the other hand, provides the isoxazoline-4,5-dicarboxylic diesters according to equation (b) (see, for example, Bull. Chem. Soc. Jpn. 59 (1986) 2827–2831 and 57 (1984) 2531–2534 or Chem. Ber. 106 (1973) 3275–3290):

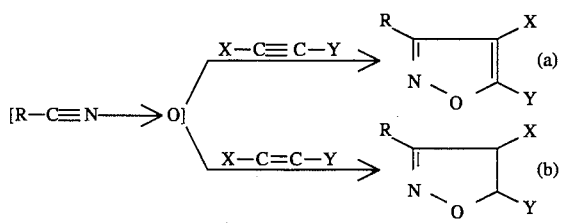

X, Y=$COOCH_3$, $COOC_2H_5$

Because the nitrile oxides IV required for the reaction are very reactive and only a few nitrile oxides which are stable substances are known, they are usually generated in situ in the reaction mixture, eg. by oxidizing corresponding aldoximes with inorganic hypochlorites according to the following equation (cf. DE-A 27 54 832; Synthesis (1982) 508):

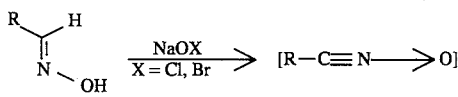

It is an object of the present invention to find an advantageous process for preparing isoxazole-4,5-dicarboxylic diesters which avoids using as starting materials the acetylenedicarboxylic diesters which are very costly and difficult to prepare. Another object is to find novel isoxazole-4,5-dicarboxylic diesters which are suitable, inter alia, as intermediates for preparing crop protection agents.

We have found that this object is achieved by a process for preparing isoxazole-4,5-dicarboxylic diesters of the formula I

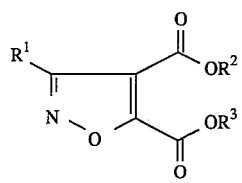

where $R^1$ is any organic radical which is inert under the reaction conditions, and $R^2$ and $R^3$ are each alkyl, cycloalkyl or benzyl, which comprises reacting an aldoxime of the formula II

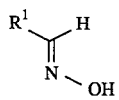

with a diester of maleic or fumaric acid, of the formula III $$R^2OOC-C=C-COOR^3 \quad \text{(III)}$$

in the presence of an aqueous solution of a hypohalite which is present in excess relative to II.

We have also found novel isoxazole-4,5-dicarboxylic diesters of the formula I'

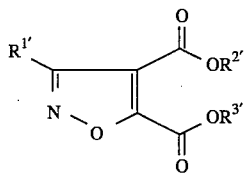

where $R^{1'}$ is $C_1$–$C_4$-alkyl which is substituted by $C_1$–$C_4$-acyloxy or $C_1$–$C_4$-alkoxycarbonyl, and $R^{2'}$ and $R^{3'}$ are each $C_1$–$C_4$-alkyl.

The process according to the invention makes it possible for the first time to prepare isoxazole-4,5-dicarboxylic diesters I from the aldoximes II and diesters of maleic or fumaric acid III according to the following equation:

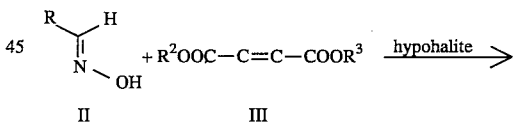

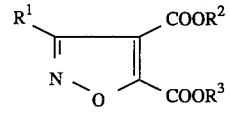

The hypohalites used in the process according to the invention are generally hypobromites and hypochlorites, preferably the latter. It is possible to use for this purpose aqueous solutions of hypochlorous or hypobromous acid, but alkali metal or alkaline earth metal hypochlorites or hypobromites are preferably employed, for example sodium, potassium, calcium, magnesium, strontium or barium hypochlorite or the corresponding hypobromites. Sodium, potassium and calcium hypochlorite are particularly preferably used, specifically in the form of their commercial aqueous solutions. If such hypohalite solutions are unavailable, they can be prepared by passing chlorine or bromine into aqueous solutions or suspensions of the hydroxides, carbonates or bicarbonates of these metals. Of course, it is also possible to use mixtures of various hypohalite solutions in the process according to the invention.

Because the hypohalites are generally added as aqueous solutions to the reaction mixture, while the diesters of maleic or fumaric acid are usually insoluble or only slightly soluble in the aqueous phase, addition thereof usually produces two phases. This is why these starting compounds are expediently dissolved in an organic solvent. It is possible to use for this purpose both solvents which are immiscible with the aqueous phase and those which dissolve in both phases, the organic and the aqueous, and in this way produce a homogeneous reaction medium. It is generally expedient to employ a two-phase system.

Examples of solvents suitable for the process according to the invention are alcohols such as methanol, ethanol, propanol or isopropanol, ketones such as acetone or methyl ethyl ketone, ethers such as diethyl ether, methyl tert-butyl ether, tetrahydrofuran or dioxane, hydrocarbons such as pentane, hexane, cyclohexane, petroleum ether, white oils or naphtha, halogenated aliphatic hydrocarbons such as methylene chloride, chloroform, tetrachloromethane, dichloroethane, trichloroethane, tetrachloroethane or perchloroethane, aromatic compounds such as benzene, toluene, xylenes or chlorobenzenes, esters such as ethyl acetate, and dimethylformamide, N-methylpyrrolidone, dimethyl sulfoxide, sulfolane etc. Of course, it is also possible to use solvent mixtures.

If water-insoluble solvents are used, it may prove advantageous for the course and result of the reaction to add to the reaction medium phase-transfer catalysts, eg. quaternary ammonium or phosphonium salts, for example triethylbenzylammonium chloride, trimethylbenzylammonium bromide, triphenylbenzylammonium chloride, methyltributylammonium iodide, tetrabutylammonium bisulfate, tetrabutylammonium chloride, tetrabutylammonium bromide or benzyltributylphosphonium bromide, in amounts of, in general, from 0.1 to 10 g/l of reaction mixture. It is expedient in the case of such two-phase or multi-phase systems to stir the reaction mixture particularly vigorously.

The temperature at which the reaction is carried out can vary within wide limits. As a rule, the reaction takes place even at −15° C. or below, and the upper temperature limit is determined in principle only by the boiling point of the solvent used, because the reaction is expediently carried out under atmospheric pressure. The reaction is preferably carried out at from 0° to 40° C. and can be carried out under elevated pressure, especially autogenous pressure, but atmospheric pressure is preferred.

It is often expedient to add buffer substances to the reaction medium in order to ensure that the process according to the invention succeeds and to prevent side reactions, because otherwise there may be hydrolysis of the esters owing, for example, to the alkalinity of the hypochlorite solution as prepared being too high. It is generally sufficient to carry out the reaction in such a way that the pH of the aqueous phase in a two-phase system is in the range of about 5 to 11, and this also applies to the pH of a homogeneous aqueous/organic reaction mixture.

The buffer systems which can be used are in principle all those able to display their buffering action in the stated pH range. However, it is preferable to use conventional buffer substances such as sodium bicarbonate, sodium acetate or the sodium dihydrogen phosphate/disodium hydrogen phosphate system. The buffer substances can be added to the reaction mixture as solids, but solutions are more expedient.

The buffer solutions can in principle have any desired concentration but, in order to avoid handling excessive quantities of liquid, generally from 0.01 to 1 molar solutions are used.

It is expedient for the desired pH of the aqueous phase or of the aqueous/organic solution to have been adjusted with the buffer, as solid or solution, before addition of the hypohalite. Subsequently, during the addition of hypohalite, it is advantageous to check the pH continuously and, if necessary, maintain the desired pH range by adding further buffer or acids or alkalis.

It may prove advantageous in the reaction of sensitive, ie. particularly reactive, starting compounds II and/or III to introduce only one of these substances into the buffered medium and then to meter in the other reactants together with the hypohalite. Another possibility in this case is to introduce one of the reactants II or III completely and the second reactant only in a small quantity, for example one tenth of the amount required, and to add the remainder of this reactant together with the hypohalite to the reaction mixture. It is advantageous to control the addition of the hypohalite solution so that there is never a high concentration of hypohalite and nitrile oxide in the reaction mixture.

The isoxazole-4,5-dicarboxylic diesters I are expediently prepared by reacting equimolar amounts of the aldoxime II and of the diester of maleic or fumaric acid III with the hypohalite. In some cases it may prove beneficial to employ an excess of diester III, for example twice the molar quantity of aldoxime, in which case unreacted component III is usually recovered subsequently.

The hypohalite is used in excess relative to the aldoxime II. As a rule, at least 1.5 moles of hypohalite per mole of II are used, advantageously at least two equivalents. It is often advantageous to use 2 to 3 moles of hypohalite per mole of aldoxime II.

It may be advantageous for technical reasons to limit the conversion by using less than the stoichiometric amount of hypohalite, for example from 150 to 190 mol-% thereof, relative to II. It is likewise possible to use more or less than the stoichiometric amount of reactant II or III.

The usual procedure for the reactions is to introduce all the components of the reaction system excepting the hypohalite into the aqueous/organic medium and then to add the hypohalite solution to this vigorously stirred mixture while monitoring the pH continuously. The optimal rate of hypohalite addition depends in general on the reactivity of the reactants and is expediently determined in a preliminary experiment.

Otherwise, the process according to the invention requires no special technical measures so that details thereof are unnecessary. The process can also be carried out continuously in a conventional manner by using tube reactors or agitated vessel cascades. Because the isoxazole derivatives I are generally preferentially soluble in organic solvents, the reaction mixture can be worked up to isolate the isoxazole-4,5-dicarboxylic diesters in a conventional manner by extraction, distillation or crystallization. Excess hypohalite, which may interfere with working up, can be decomposed by reduction with, for example, iron(II) sulfate, or thiosulfates or sulfites.

The aldoximes II required for the process according to the invention are either known or can easily be prepared by generally known processes (see, for example, Houben-Weyl, Methoden der organischen Chemie, Vol. 10/4, pages 55 to 66, Thieme; Stuttgart, 1968) by reacting the corresponding aldehydes with hydroxylamine. The aldoximes II can, of course, be used in the form both of their E and Z isomers and of mixtures thereof. The diesters of maleic or fumaric acid III are commercial products.

The process according to the invention for preparing the isoxazole-4,5-dicarboxylic diesters I has virtually universal applicability. Thus, compounds I can be obtained from the corresponding aldoximes II in which $R^1$ is an aliphatic radical with 1 to 20, a cycloaliphatic radical with 3 to 10, an aromatic radical with 6 to 10, a heteroaromatic or heterocyclic radical with 3 to 10 or an araliphatic radical with 4 to 12 carbon atoms. The top limit on the number of carbon atoms in $R^1$ is determined solely by the usefulness and utilizability of the relevant compounds and does not derive from a lack of applicability of the process according to the invention when $R^1$ is larger.

$R^1$ can also be substituted. The nature and number of the substituents can in principle be chosen as required, provided, of course, that they are chemically possible and that under the reaction conditions they are inert to the oxidizing agent, ie. the basic hypohalite solution, and to the nitrile oxide which is formed. Thus, the process according to the invention can also be used to prepare isoxazole derivatives I in which the aliphatic, araliphatic or cycloaliphatic radicals $R^1$ contain acetal or ester moieties or in which the carbon chain is interrupted by hetero atoms, especially oxygen atoms.

The nature of $R^2$ and $R^3$ which are introduced into the compound I from the diester of maleic or fumaric acid is not in general critical for the course of the reaction and, accordingly, can be chosen as required. However, it is expedient for $R^2$ and $R^3$ each to be alkyl, especially $C_1$-$C_4$-alkyl. Also suitable are $C_3$-$C_6$-cycloalkyl such as cyclopropyl, cyclobutyl, cyclopentyl or cyclohexyl, and benzyl.

$R^2$ and $R^3$ can be identical or different. If they are different, the cycloaddition of the nitrile oxide with the diester III generally results in a mixture of the regioisomers Ia and Ib

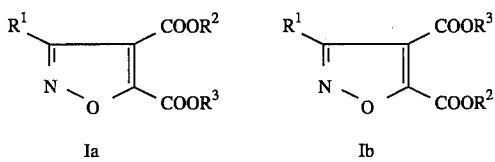

Ia          Ib in which the proportions of the regioisomers are essentially determined by the steric requirements of $R^1$, $R^2$ and $R^3$. This effect is not generally critical in view of the intended use of the compounds as intermediates, and may in some circumstances be desirable. However, it is generally preferred to convert diesters of maleic or fumaric acid III in which $R^2$ and $R^3$ are into the compounds I.

It is possible and advantageous to use the process according to the invention to prepare isoxazole- 4,5-dicarboxylic diesters I in which $R^1$ is $C_1$-$C_{10}$, in particular $C_1$-$C_6$, alkyl, $C_3$-$C_8$, in particular $C_3$-$C_7$, cycloalkyl, a 5- to 7-membered aromatic or aliphatic heterocycle containing one or two oxygen or nitrogen atoms, or phenyl or benzyl.

These $R^1$ radicals can be unsubstituted or carry substituents which are inert under the reaction conditions.

Thus, when $R^1$ is alkyl it can carry, depending on its size, 1, 2, 3, 4 or 5, preferably up to 3, identical or different substituents such as $C_3$-$C_7$-cycloalkyl, $C_1$-$C_3$-alkoxy, alkoxycarbonyl, acyloxy, alkylenedioxy, halogen, cyano or phenyl, it being possible for phenyl to be substituted by up to 3, preferably by one or two, of the following: halogen, $C_1$-$C_4$-alkyl, $C_1$-$C_4$-haloalkyl, $C_1$-$C_4$-alkoxy, -acyloxy, -alkoxycarbonyl, $C_1$-$C_4$-haloalkoxy, cyano or nitro, and the substitution pattern of these phenyl substituents not being critical in general.

When $R^1$ is alkyl this can be straight-chain or branched. It is possible and particularly advantageous to prepare according to the invention the compounds I where $R^1$ is alkyl which is substituted by $C_1$-$C_4$-alkoxy, -acyloxy, alkoxycarbonyl, halogen and/or phenyl, the phenyl being substituted by, preferably, halogen atoms and/or $C_1$-$C_4$-alkyl groups.

It is self-evident to those skilled in the art that the number of substituents depends on the number of carbon atoms in the aliphatic radical. The substitution pattern on the aliphatic radicals $R^1$ is not generally critical for the reaction according to the invention.

When $R^1$ is cycloalkyl it can, depending on its size, be substituted by 1, 2, 3, 4 or 5, preferably by up to 3, identical or different $C_1$-$C_4$-alkyl, $C_1$-$C_3$-alkoxy, -acyloxy, -alkoxycarbonyl or halogen substituents.

It is also possible advantageously to use the process according to the invention to prepare isoxazole- 4,5-dicarboxylic diesters in which $R^1$ is a 5- to 7-membered heterocycle which can be substituted by 1 to 3 identical or different $C_1$-$C_4$-alkyl, $C_1$-$C_4$-alkoxy, $C_1$-$C_4$-alkoxycarbonyl and/or -acyloxy, particularly preferably $C_1$-$C_4$-alkyl groups. When $R^1$ is a heterocycle it can be aromatic or aliphatic in nature. When $R^1$ is heteroaromatic it can contain one or two oxygen and/or nitrogen atoms. It is possible and advantageous to use the process according to the invention to prepare, for example, the isoxazole derivatives I in which $R^1$ is substituted or unsubstituted pyridyl, pyrazinyl, pyrimidinyl, pyridazinyl, pyrazolyl, imidazolyl, oxazolyl or isoxazolyl.

It is likewise possible advantageously to prepare isoxazole derivatives I according to the invention in which $R^1$ is a 5- to 6-membered aliphatic heterocycle which contains 1 or 2 nitrogen and/or, preferably, oxygen atoms. Examples of such aliphatic heterocyclic radicals $R^1$ are substituted or unsubstituted tetrahydrofuryl, tetrahydropyranyl, 1,3-dioxolanyl, 1,3-dioxanyl, 1,4-dioxanyl, oxepanyl, 1,3-dioxepanyl, 1,4-dioxepanyl, 1,5-dioxepanyl, pyrrolidinyl, imidazolidinyl, piperidinyl or piperazinyl.

It is also possible and advantageous to use the process according to the invention to prepare isoxazole derivatives I in which $R^1$ is substituted or unsubstituted $C_6$-$C_{10}$-aryl or $C_7$-$C_{12}$-aralkyl, especially phenyl or benzyl. The aryl radicals, especially phenyl, can carry 1, 2 or 3 identical or different $C_1$-$C_6$-alkyl, $C_1$-$C_6$-haloalkyl, $C_1$-$C_6$-alkoxy, -alkoxycarbonyl, -acyloxy, $C_1$-$C_6$-haloalkoxy, halogen, nitro or cyano substituents.

It is also possible and advantageous to use the process according to the invention to prepare, in particular, the novel isoxazole-4,5-dicarboxylic diesters of the formula I'

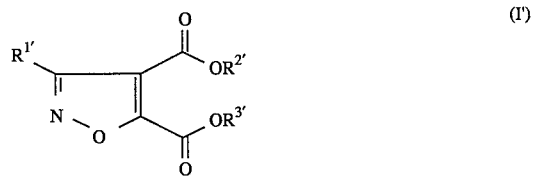

where $R^{1'}$ is $C_1$-$C_4$-alkyl which is substituted by $C_1$-$C_4$-acyloxy or $C_1$-$C_4$-alkoxycarbonyl, and $R^{2'}$ and $R^{3'}$ are each $C_1$-$C_4$-alkyl. The conversion of isoxazole-4,5-dicarboxylic diesters into herbicidal isoxazole-5-carboxamides is described, for example, in DE-A 38 12 225.

EXAMPLE 1

A mixture of 18.3 g (0.21 mol) of isobutyraldoxime, 7.1 g (0.04 mol) of disodium hydrogen phosphate dihydrate, 100 ml of methylene chloride, 28.8 g (0.2 mol) of dimethyl fumarate and 100 ml of water is cooled to 10° C. While stirring vigorously, 267 g of a 13.4% strength sodium hypochlorite solution (0.48 mol) are added dropwise over the course of 2 hours to this mixture, which is then stirred at 20° C. for 15 hours. The organic phase is separated off, the aqueous phase is extracted with methylene chloride, and the organic phases are combined, dried over sodium sulfate and concentrated under reduced pressure. The crude product is purified by distillation.

30 g of dimethyl 3-isopropylisoxazole-4,5-dicarboxylate, boiling point 102° C. 0.4 mbar are obtained.

Yield: 66% of theory.

$^1$H-NMR (CDCl$_3$): 1.4(d,6H);3.2–3.5(m, 1H);3.9(s,3H); 4.0(s,3H).

EXAMPLE 2

A mixture of 18.3 g (0.21 mol) of isobutyraldoxime, 1.11 g (0.004 mol) of tetrabutylammonium chloride, 3.5 g (0.02 mol) of disodium hydrogen phosphate dihydrate, 3.1 g (0.02 mol) of sodium dihydrogen phosphate dihydrate, 28.8 g (0.2 mol) of dimethyl fumarate, 100 ml of methylene chloride and 100 ml of water is cooled to 10° C. While stirring vigorously, 278 g of a 13.4% strength sodium hypochlorite solution (0.5 mol) are added dropwise over the course of two hours, and the mixture is then stirred at 20° C. for two hours.

Working up and purification are carried out as in Example 1.

Yield of dimethyl 3-isopropylisoxazole-4,5-dicarboxylate: 38 g, corresponding to 84% of theory.

EXAMPLE 3

A mixture of 87 g (1.0 mol) of isobutyraldoxime, 17.8 g (0.1 mol) of disodium hydrogen phosphate dihydrate, 15.6 g of sodium dihydrogen phosphate dihydrate, 8.3 g (0.03 mol) of tetrabutylammonium chloride, 288 g (2.0 mol) of dimethyl maleate, 500 ml of methylene chloride and 500 ml of water is cooled to 10° C. While stirring vigorously, 1,390 g of a 13.4% strength sodium hypochlorite solution are added dropwise over the course of 4 hours, and then the mixture is stirred at 20° C. for 16 hours.

The organic phase is separated off, the aqueous phase is extracted twice with methylene chloride, and the combined organic phases are dried over sodium sulfate and concentrated under reduced pressure.

Distillation results in 184 g of dimethyl 3-isopropylisoxazole-4,5-dicarboxylate, boiling point 99° C./0.3 mbar (81% of theory). A previous fraction contains 140 g of dimethyl maleate (0.97 mol) which can be returned to the reaction.

EXAMPLES 4 TO 21

General procedure

A mixture of 0.5 mol of aldoxime, 6.9 g (0.025 mol) of tetrabutylammonium chloride, 8.9 g (0.05 mol) of disodium hydrogen phosphate dihydrate, 7.8 g (0.05 mol) of sodium dihydrogen phosphate dihydrate, 75.6 g (0.525 mol) of dimethyl fumarate, 250 ml of methylene chloride and 250 ml of water is cooled to 10° C. While stirring vigorously, 667 g of a 13.4% strength sodium hypochlorite solution (1.2 mol) are added dropwise over the course of 3 hours, and then the mixture is stirred at 20° C. for 16 hours.

The organic phase is separated off, the aqueous phase is extracted twice with methylene chloride, and the combined organic phases are washed three times with water, dried over sodium sulfate and concentrated under reduced pressure.

The crude products are, if volatile, purified by distillation. In the case of involatile products, the low boiling fractions are removed by distillation, which usually results in the products in a purity of more than 95% (determined by gas chromatography).

The results of the reactions are listed in the table. This table contains the list of isoxazole derivatives I prepared plus data on the yield, the melting point (m.p.) if the compounds were crystalline, or the boiling point (b.p.) if the products were distilled, and the principle data in the 250 MHz $^1$H-NMR spectra of these compounds in deuterochloroform (CDCl$_3$).

The following abbreviations are used in the table:

Me: methyl;

Et: ethyl;

iPr: isopropyl;

c-Pr: cyclopropyl;

t-Bu: tert-butyl;

Ph: phenyl;

s: singlet;

d: doublet;

t: triplet;

q: quartet;

m: multiplet

TABLE

| | | Isoxazole-4,5-dicarboxylic diesters | | | |
|---|---|---|---|---|---|
| Example | R$^1$ | R$^2$ = R$^3$ | Yield | m.p./b.p. | $^1$H-NMR (CDCl$_3$) |
| 4 | Me | Me | 78% | 34–35° C. | 2.5(s, 3H), 3.9(s,3H), 4.0(s, 3H). |
| 5 | Et | Me | 83% | 115° C./0.5 mbar | 1.3(t, 3H), 2.9(q, 2H), 3.9(s, 3H), 4.0(s, 3H). |
| 6 | c-Pr | Me | 75% | | 0.9–1.2(m, 4H), 2.1–2.4(m, 1H), 3.9(s, 3H), 4.0(s, 3H). |
| 7 | t-Bu | Me | 89% | 99–101° C./0.3 mbar | 1.4(s, 9H), 3.9(s, 3H), 3.95(s, 3H). |
| 8 | 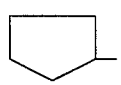 | Me | 82% | | 1.6–2.2(m, 8H), 3.3–3.5(m, 1H), 3.9(s, 3H), 4.0(s,3H). |
| 9 |  | Me | 58% | 120° C./0.2 mbar | 1.6(d, 3H), 3.35(s, 3H), 3.9(s, 3H), 4.0(s, 3H), 4.7(q, 1H). |

TABLE-continued

Isoxazole-4,5-dicarboxylic diesters

| Example | R¹ | R²=R³ | Yield | m.p./b.p. | ¹H-NMR (CDCl₃) |
|---|---|---|---|---|---|
| 10 | (tetrahydrofuran-2-yl) | Me | 63% | | 1.8–2.5(m, 2H), 3.9(s, 3H), 4.0(s, 3H), 3.7–4.3(m, 5H). |
| 11 | (tetrahydropyran-4-yl) | Me | 80% | | 1.8–2.1(m, 4H), 3.2–3.4(m, 1H), 3.4–3.6(m, 2H), 3.9(s, 3H), 4.0(s, 3H), 4.0–4.2(m, 2H). |
| 12 | CH(OMe)₂ | Me | 45% | | 3.5(s, 6H), 3.9(s, 3H), 4.0(s, 3H), 5.7(s, 1H). |
| 13 | 4-F-C₆H₄-CH₂- | Me | 78% | | 3.8(s, 3H), 4.0(s, 3H), 4.2(s, 2H), 6.9–7.1(m, 2H), 7.1–7.4(m, 2H). |
| 14 | Ph | Me | 90% | | 3.8(s, 3H), 4.0(s, 3H), 7.3–7.6(m, 3H), 7.6–7.8(m, 2H). |
| 15 | o-tolyl | Me | 85% | | 2.3(s, 3H), 3.8(s, 3H), 4.0(s, 3H), 7.2–7.5(m, 4H). |
| 16 | 2,4-Cl₂-C₆H₃- | Me | 85% | | 3.8(s, 3H), 4.0(s, 3H), 7.3–7.6(m, 3H). |
| 17 | 2-pyridyl | Me | 59% | | 3.95(s, 3H), 4.0(s, 3H), 7.4(m, 1H), 7.8(dt, 1H), 8.1(d, 1H), 8,7(d, 1H). |
| 18 | 3-isopropyl-5-methylisoxazol-yl | Me | 61% | | 1.3(d, 6H), 3.0–3.2(m, 1H), 3.9(s, 3H), 4.0(s,3H), 6.9(s, 1H). |
| 19 | Cl-(CH₂)₃- | Me | 85% | | 2.1–2.3(m, 2H), 3.1(t, 2H), 3.6(t, 2H), 3.9(s, 3H), 4.0(s, 3H). |
| 20 | CH₃C(O)OCH₂- | Me | 48% | | 2.1(s, 3H), 3.9(s, 3H), 4.0(s, 3H), 5.4(s, 2H). |
| 21 | CH₃C(O)OCH(CH₃)- | Me | 59% | | 1.7(d, 3H), 2.1(s, 3H), 3.9(s, 3H), 4.0(s, 3H), 6.2(q, 1H). |

We claim:

1. A process for preparing an isoxazole- 4,5-dicarboxylic diester of the formula I

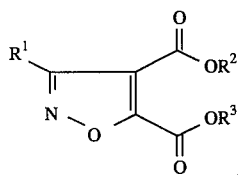

where R¹ is

C₁–C₁₀ alkyl which is unsubstituted or substituted by 1 to 5 substituents selected from the group consisting of C₃–C₇-cycloalkyl, C₁–C₄-alkoxy-, -alkoxycarbonyl, -acyloxy, -alkylenedioxy, halogen, cyano or phenyl, it being possible for phenyl to be substituted by up to 3, of the following: halogen, C₁–C₄-alkyl, C₁–C₄-haloalkyl, C₁–C₄-alkoxy, -acyloxy, -alkoxycarbonyl, C₁–C₄-haloalkoxy, cyano or nitro;

C₃–C₇-cycloalkyl which is unsubstituted or substituted by 1 to 5 identical or different C₁–C₄-alkyl, C₁–C₃-alkoxy, -acyloxy, -alkoxycarbonyl or halogen substituents;

phenyl or, which may carry 1, 2 or 3 identical or different C₁–C₆-alkyl, C₁–C₆-haloalkyl, C₁–C₄-alkoxy, -alkoxycarbonyl, -acyloxy, C₁–C₆-haloalkoxy, halogen, nitro or cyano substituents at the aromatic ring;

a 5- to 7-membered heterocyclic selected from the group consisting of pyridyl, pyrazinyl, pyrimidinyl, pyridazinyl, pyrazolyl, imidazolyl, oxazolyl or isoxazolyl, tetrahydrofuryl, tetrahydropyranyl, 1,3-dioxolanyl, 1,3-dioxanyl, 1,4-dioxanyl, oxepanyl, 1,3-dioxepanyl, 1,4-dioxepanyl, 1,5-dioxepanyl, pyrrolidinyl, imidazolidinyl, piperidinyl or piperazinyl which may carry 1 to 3 identical or different $C_1$–$C_4$-alkyl, $C_1$–$C_4$-alkoxy, $C_1$–$C_4$-alkoxycarbonyl, -acyloxy or $C_1$–$C_4$-alkyl groups, and $R^2$ and $R^3$ are each alkyl, cycloalkyl or benzyl, which consists essentially of reacting an aldoxime of the formula II

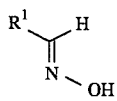 (II)

with a diester of maleic or fumaric acid, of the formula III

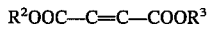 (III)

where $R^2$ and $R^3$ are identical or different and have the abovementioned meanings, in the presence of an aqueous solution of a hypohalite which is present in excess relative to II.

2. A process as defined in claim 1, wherein sodium hypochlorite, potassium hypochlorite or calcium hypochlorite is used as hypohalite.

3. A process as defined in claim 1, wherein 2 to 3 moles of the hypohalite are used per mole of aldoxime II.

4. A process as defined in claim 1, wherein the reaction is carried out in an organic/aqueous two-phase system.

5. A process as defined in claim 1, wherein the reaction is carried out at from 0° to 40° C.

6. A process as defined in claim 1, wherein the reaction is carried out at a pH in the range from 5 to 11.

7. A process as defined in claim 1, wherein $R^1$ is $C_1$–$C_4$-alkyl which is substituted by $C_1$–$C_4$-acyloxy or $C_1$–$C_4$-alkoxycarbonyl and $R^2$ and $R^3$ are each $C_1$–$C_4$-alkyl.

* * * * *

UNITED STATES PATENT AND TRADEMARK OFFICE
CERTIFICATE OF CORRECTION

PATENT NO.: 5,473,069

DATED: December 5, 1995

INVENTOR(S): KUEKENHOEHNER et al.

It is certified that error appears in the above-identified patent and that said Letters Patent is hereby corrected as shown below:

Column 10, claim 1, line 66, "$C_1$-$C_4$-alkoxy" should be --$C_1$-$C_6$-alkoxy--.

Signed and Sealed this

Twentieth Day of February, 1996

Attest:

BRUCE LEHMAN

*Attesting Officer*     Commissioner of Patents and Trademarks